(12) United States Patent
Sacherer et al.

(10) Patent No.: US 7,740,599 B2
(45) Date of Patent: Jun. 22, 2010

(54) MAGAZINE FOR ANNULARY CAPILLARY LANCETS

(75) Inventors: Klaus-Dieter Sacherer, Kirchheim (DE); Ronald Mönch, Ilvesheim (DE); Michael Schabbach, Weinheim (DE); Jörg Scherer, Ludwigshafen (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 698 days.

(21) Appl. No.: 11/178,810

(22) Filed: Jul. 11, 2005

(65) Prior Publication Data

US 2006/0008389 A1 Jan. 12, 2006

Related U.S. Application Data

(63) Continuation of application No. PCT/EP2004/000117, filed on Jan. 10, 2004.

(30) Foreign Application Priority Data

Jan. 23, 2003 (DE) ................. 103 02 501

(51) Int. Cl.
*A61B 5/00* (2006.01)
(52) U.S. Cl. ................. 600/583; 606/181; 606/183
(58) Field of Classification Search ............. 600/583; 606/181, 182
See application file for complete search history.

(56) References Cited

U.S. PATENT DOCUMENTS

| | | | |
|---|---|---|---|
| 4,794,926 A | 1/1989 | Munsch et al. | |
| 4,823,806 A | 4/1989 | Bajada | |
| 5,284,156 A * | 2/1994 | Schramm et al. | 600/567 |
| 5,510,266 A | 4/1996 | Bonner et al. | |
| 5,526,822 A * | 6/1996 | Burbank et al. | 600/567 |
| 5,632,410 A | 5/1997 | Moulton et al. | |
| 5,829,589 A | 11/1998 | Nguyen et al. | |
| 5,971,941 A | 10/1999 | Simons et al. | |
| 6,036,924 A | 3/2000 | Simons et al. | |
| 6,099,484 A * | 8/2000 | Douglas et al. | 600/583 |
| 6,159,424 A | 12/2000 | Kauhaniemi et al. | |
| 6,234,062 B1 * | 5/2001 | Griffin | 92/23 |
| 6,332,871 B1 * | 12/2001 | Douglas et al. | 600/583 |

(Continued)

FOREIGN PATENT DOCUMENTS

DE 28 03 345 B1 6/1979

(Continued)

OTHER PUBLICATIONS

Roche Diagnostics, Accu-Chek (R) Compact Owner's Booklet, 2004.

*Primary Examiner*—Max Hindenburg
*Assistant Examiner*—Michael C Stout
(74) *Attorney, Agent, or Firm*—Woodard, Emhardt, Moriarty, McNett & Henry LLP

(57) ABSTRACT

A device for receiving a body fluid for analysis, comprising a container and at least one sample-receiving unit which can be impinged upon by the body fluid at a receiving point and which can be extracted from a guide chamber of the container by means of a drive unit. According to the invention, a coupling device is provided in order to couple the sample receiving unit to the drive unit to ensure back and forth movement between the guide chamber and the receiving point.

35 Claims, 9 Drawing Sheets

U.S. PATENT DOCUMENTS

| | | |
|---|---|---|
| 6,375,627 B1 * | 4/2002 | Mauze et al. .................. 600/584 |
| 6,472,220 B1 | 10/2002 | Simons et al. |
| 6,497,845 B1 | 12/2002 | Sacherer |
| 6,616,616 B2 | 9/2003 | Fritz et al. |
| 6,706,159 B2 | 3/2004 | Moerman et al. |
| 6,827,899 B2 | 12/2004 | Maisey et al. |
| 2002/0177787 A1 | 11/2002 | Duchon et al. |
| 2002/0188223 A1 * | 12/2002 | Perez et al. .................. 600/573 |
| 2003/0050573 A1 | 3/2003 | Kuhr et al. |
| 2003/0144608 A1 | 7/2003 | Kojima et al. |
| 2003/0153939 A1 | 8/2003 | Fritz et al. |
| 2003/0212347 A1 | 11/2003 | Sohrab |
| 2003/0223906 A1 | 12/2003 | McAllister et al. |
| 2004/0009100 A1 | 1/2004 | Simons et al. |
| 2004/0034318 A1 * | 2/2004 | Fritz et al. ..................... 604/19 |
| 2004/0133127 A1 * | 7/2004 | Roe et al. ..................... 600/583 |
| 2006/0052723 A1 * | 3/2006 | Roe .............................. 600/583 |

FOREIGN PATENT DOCUMENTS

| | | |
|---|---|---|
| DE | 198 54 316 A1 | 10/1999 |
| DE | 100 53 974 A1 | 5/2002 |
| EP | 0 301 165 A2 | 2/1989 |
| WO | WO 97/46887 A1 | 12/1997 |
| WO | WO-02/36010 A1 * | 5/2002 |
| WO | WO 02/056751 A2 | 7/2002 |

* cited by examiner

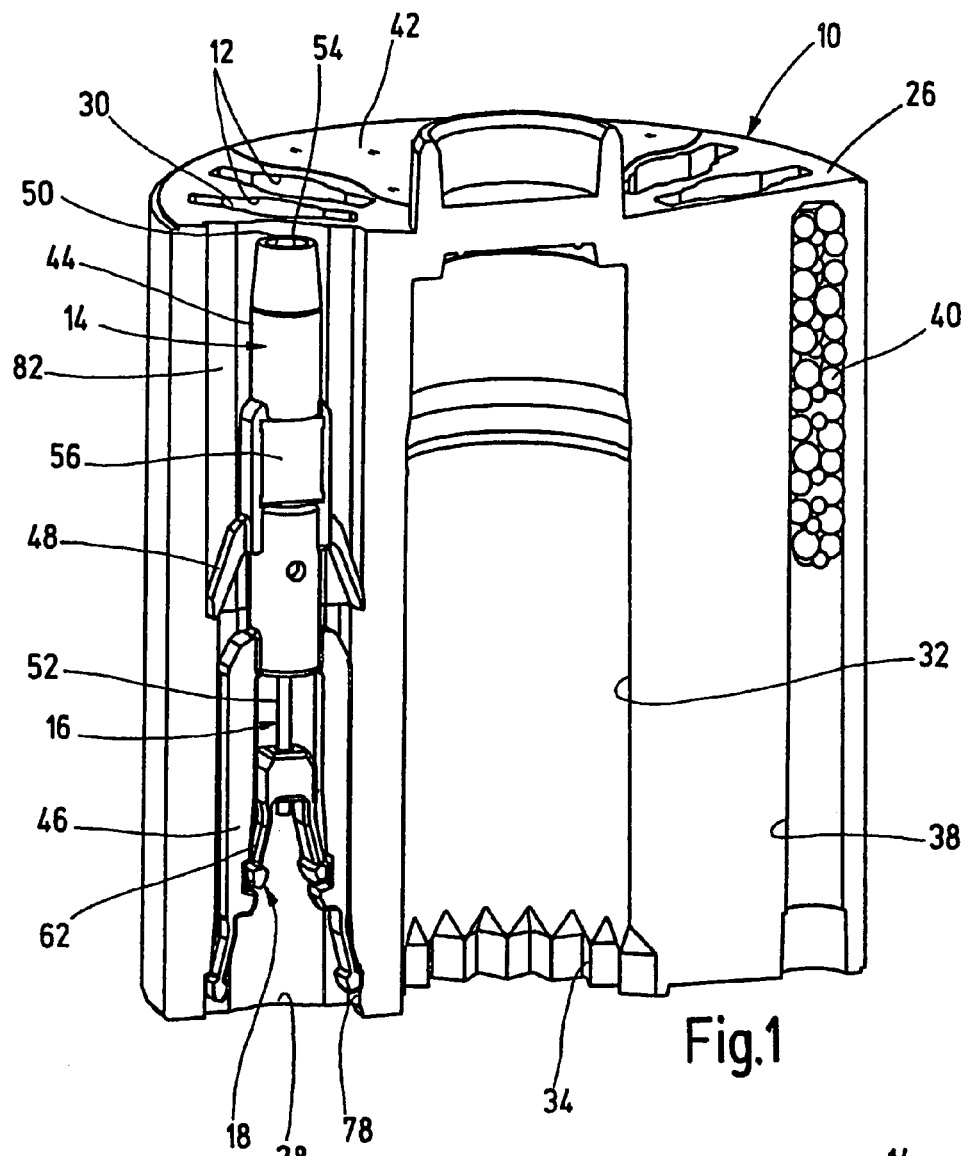
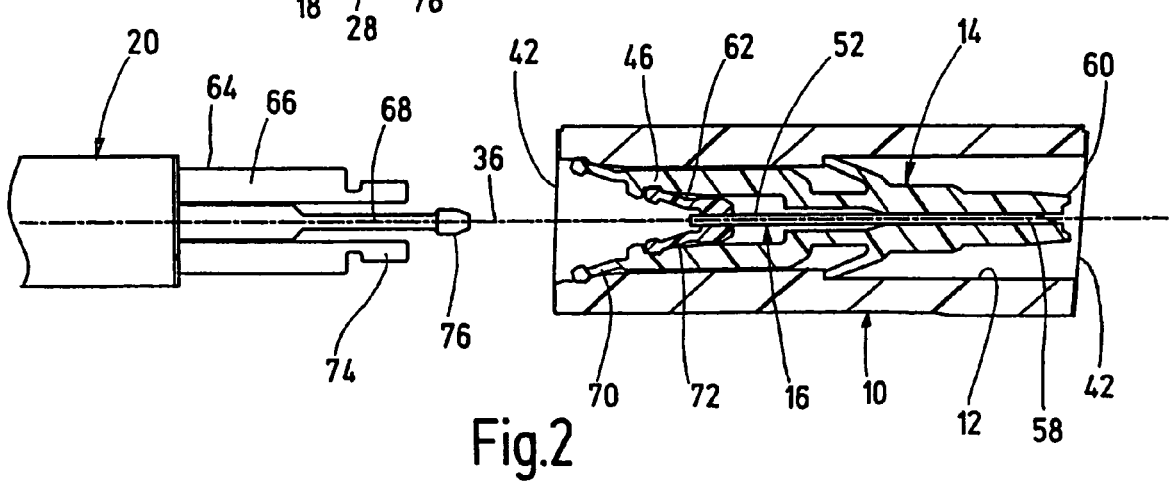
Fig.1
Fig.2

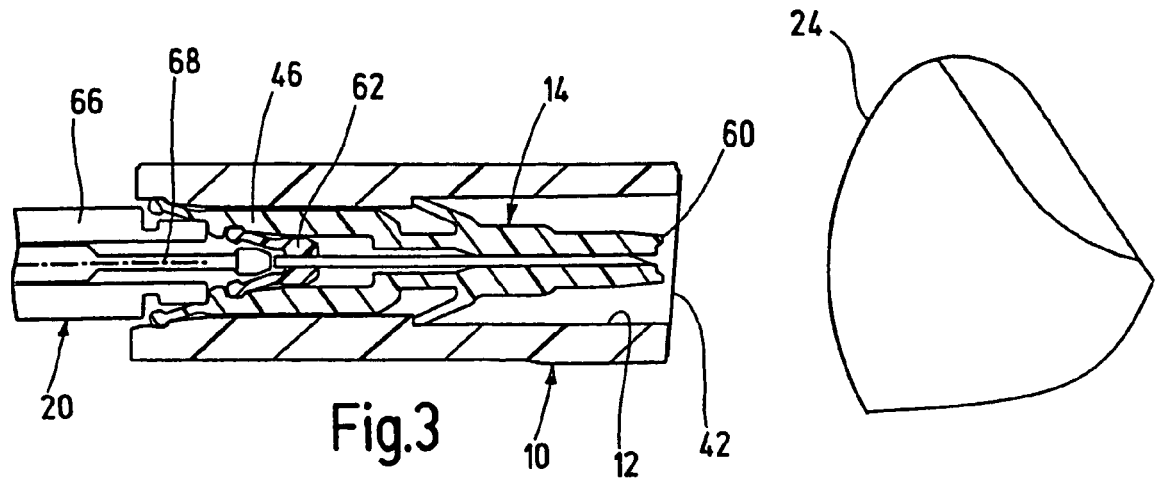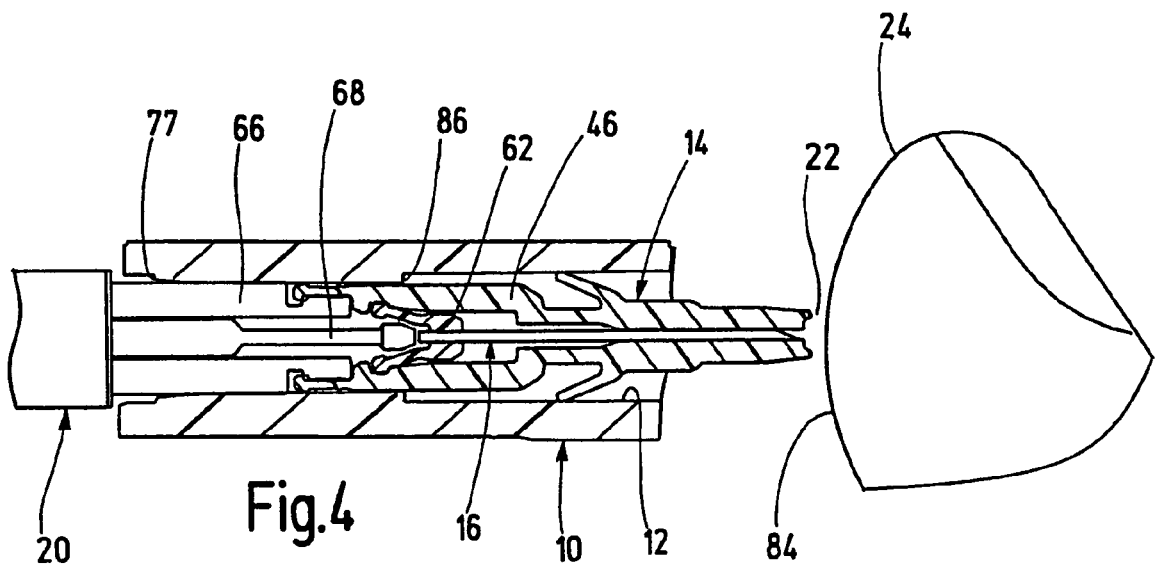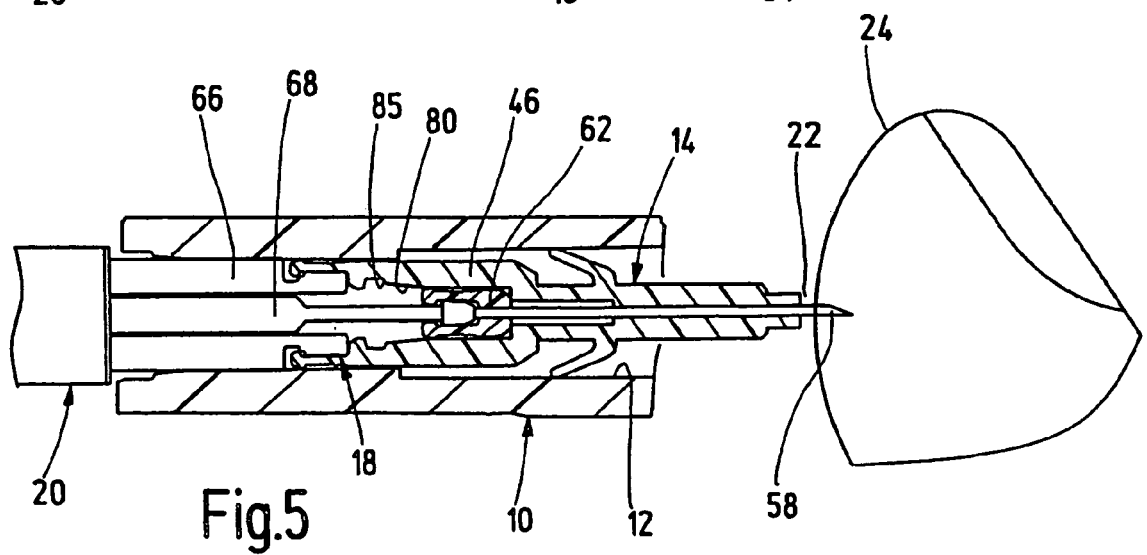

MAGAZINE FOR ANNULARY CAPILLARY LANCETS

REFERENCE TO RELATED APPLICATIONS

The present application is a continuation of International Patent Application No. PCT/EP2004/000117 filed Jan. 10, 2004, which claims foreign priority to German Patent Application 103 02 501.4 filed Jan. 23, 2003, which are hereby incorporated by reference in their entirety.

BACKGROUND

The invention concerns a device and a method for receiving a body fluid for analysis according to the preamble of the independent patent claims.

Single-use or rapid tests are known for patient self monitoring especially in the case of diabetic diseases in which small amounts of a body fluid are applied to an analytical test element in order to determine a metabolic quantity in an automated measuring process. Spring-driven lancing aids for collecting capillary blood have been developed especially for the blood glucose determination which are for example placed on a finger pad by the user in order to collect a sufficient amount of blood for the subsequent analysis by a puncture that should cause as little pain as possible. The blood which comes out is dabbed onto a test strip as a sample receiving unit which is ejected from a measuring instrument and this test strip is discarded as a consumable after the measurement is completed. Apart from the detailed steps which are still time-consuming, a particular problem in this field is the risk of contamination or infection by the uncontrolled release of consumables into the environment.

Based on this, the object of the invention is to avoid the disadvantages occurring in the prior art and to optimize a system or method of the above-mentioned type to enable a simple and substantially situation-independent operation even for laymen and to ensure a particularly hygienic handling.

SUMMARY

The combination of features stated in each of the independent patent claims is proposed to achieve this object. Advantageous embodiments and further developments of the invention are derived from the dependent claims.

The invention is based on the idea of driving a sample receiving unit as such and to furnish it with suitable elements for this purpose. Accordingly a coupling device is proposed according to the invention for coupling the sample receiving unit to the drive unit for a forwards and backwards movement between the guide chamber and the receiving site. Hence the user does not have to touch the sample receiving unit but can allow this to be automatically performed by the system. As a result, the measurement can be accelerated and carried out with a high degree of reliability and safety, and by recassetting or return into the container, it is possible to ensure a hygienic handling and disposal. For the patient it means a considerable simplification not least because it can be used discreetly without at once for example being recognized as a diabetic.

Another improvement in this regard is achieved by the coupling device preferably having automatically operating connecting means to make and disengage a form-fitting connection between the drive unit and sample receiving unit whereby the drive unit and sample receiving unit are separated from one another in a starting position. This can be advantageously achieved by the coupling device having at least one engaging means that can be moved between a release position and an engaging position in a distance-dependent manner during the forwards and backwards movement in order to couple the drive unit and sample receiving unit. For a self-controlled process, it is advantageous when the coupling device has a guide block and in particular one that is formed by an inclined bevel of the guide chamber that can be tracked by the engaging means.

The engaging means is advantageously located at a proximal end of the sample receiving unit and formed by at least one holding claw that can be shifted into an engaging position under its own tension. A mechanically particularly simple embodiment provides that the drive unit has a plunger and that the engaging means automatically engages the head member of the plunger when the plunger is advanced axially.

A special aspect of the invention consists of a hooked plunger as a coupling device that can be hooked onto the sample receiving unit. With regard to the forwards and backwards movement, an advantageous embodiment provides that the hooked plunger has a thrusting flank that butts against the sample receiving unit. In order to return the sample receiving unit, it is advantageous when the hooked plunger has a pulling flank that can engage with the sample receiving unit. In order to facilitate the latching and unlatching, it is advantageous when the pulling and/or pushing flank are sloped towards their free lateral edge in the direction of the forwards movement.

In order to achieve a reliable coupling, it is advantageous when the hooked plunger has a cranked hook head such that the hook head protrudes laterally when it couples to the sample receiving unit. Another improvement results from the fact that the hooked plunger can be pivoted relative to the sample receiving unit by means of a bevelled part of the plunger that moves against a guide contour during the forwards and backwards movement. In this connection, it is advantageous when the hooked plunger is guided in a tapered guide sleeve which tapers in the direction of the forwards movement where the tapered guide is eccentrically displaced relative to the central axis of the guide chamber.

In order to facilitate the piercing of a protective foil and the movement into the engaging position, it is advantageous when the hooked plunger has a spike-like prolongation pointing towards the guide chamber that is shaped on the head of the hooked plunger.

In order to facilitate the latching and to ensure a defined securing of the sample receiving unit after it has been returned, it is advantageous when the sample receiving unit is held in a detachable manner by a clamping structure projecting into the guide chamber where the clamping force of the clamping structure should be less than the maximum drive force of the drive unit. In this connection it is advantageous for a space-saving construction when the sample receiving unit has a proximal end section that can be elastically deformed in the clamping structure to open a passage cross-section of the guide chamber in order to latch and/or unlatch the hooked plunger. In order to achieve this, it is advantageous when the clamping structure has two guide ribs which run parallel to one another along the guide chamber and two projecting clamping cams located in a clamping area of the guide chamber facing the drive unit that are preferably laterally displaced relative to the guide ribs.

The sample receiving unit advantageously has a recess as a coupling element to hook the hooked plunger.

Another aspect of the invention is that a lancing unit is integrated into the sample receiving unit to carry out a lancing movement towards a body part containing the body fluid. The puncture and sample collection can thus take place simply and hygienically in an automated sequence of movements while avoiding any handling by the user.

For a particularly advantageous telescope-like movement, it is advantageous when the lancing unit can be displaced in a guide of the sample receiving unit in its direction of movement. In this connection the collection of body fluid can be optimized in such a manner that the lancing unit pierces the body part at a predetermined distance to a free front area or receiving area of the sample receiving unit.

For a separate movement control, it is advantageous when the lancing unit can be coupled in a form-fitting manner with the drive unit by means of an allocated engaging means of the coupling device for a reciprocating lancing movement. A particularly advantageous constructional design provides that the drive unit has a double plunger formed by an outer plunger and an inner plunger that can be longitudinally displaced therein.

In order to control the sequence of movement of the sample receiving unit and/or lancing unit, the drive unit advantageously has a control device. In order to control a relative movement, it is also possible that the sample receiving unit has limit stops for the lancing unit preferably formed by projecting edges of the body.

Another advantageous embodiment provides that the lancing unit can be displaced to a limited extent relative to the sample receiving unit against the restoring force of a spring member.

For a sequence of movement that is as energy saving as possible, it is advantageous when the sample receiving unit can be moved in a sliding guide of the guide chamber.

In order to further improve the guidance and centering at the intended site of collection, it is advantageous when the sample receiving unit is held preferably by means of a detent connection on a carriage that can be moved backwards and forwards in the guide chamber by means of the drive unit.

The sample receiving unit advantageously has a preferably capillary-active transport channel for a flow connection that is largely self-acting from the collection site to an evaluation site which can comprise a special analytical test element for examining the body fluid on the sample receiving unit.

Another advantageous embodiment provides that the transport channel is formed by a ring slot between a lancet and a wall area of the sample receiving unit surrounding the lancet. In order to favourably support the liquid transport, it is advantageous when the ring-shaped transport channel has a widened cross-section in a transport area that faces away from the bearing side of the lancet that is loaded by gravity.

In this connection it is favourable when the transport channel discharges onto an analytical test field via a lateral outlet opening preferably in the transport area. It is also possible that the transport channel discharges onto an analytical test sleeve via an axial outlet opening pointing in the direction of the channel.

In order to protect against damaging environmental influences, it is favourable when the guide chamber is closed by a sealing foil at least in the area of an ejection opening. In this connection the sample receiving unit should have a free end area facing the direction of propulsion to pierce the sealing foil in order to prevent damage to the lancing unit.

The sample receiving unit is advantageously designed as a test strip or preferably as an injection-molded test body in particular for examining blood. Another advantageous variant provides that the sample receiving unit is formed by a hollow needle to suck in the sample fluid which is preferably at the same time designed as a guide for the lancing unit.

In order to make it easier to operate, it is advantageous when the container is designed as a magazine for storing a plurality of sample receiving units. In an embodiment that is advantageous for controlling the movement, the container as a drum magazine can have a plurality of guide chambers running axially each for one sample receiving unit that are distributed in the circumferential direction. Alternatively, a particularly compact design provides that the container as a disk magazine has a plurality of radial guide chambers each for one sample receiving unit that are arranged radially.

The invention also extends to an analytical instrument, in particular a transportable hand device for medical diagnostics containing a device according to the invention for receiving a body fluid as well as to sample receiving units with a form-fitting drive coupling for use in such devices.

With regard to the method, the above-mentioned object is achieved in that the sample receiving unit that can be coupled to the drive unit is retracted into the guide chamber after sample collection. The body fluid is advantageously collected in the area of the receiving site by a lancing movement of a lancing unit that can be moved in the sample receiving unit.

BRIEF DESCRIPTION OF THE DRAWINGS

The invention is further elucidated in the following on the basis of the embodiments shown schematically in the drawing.

FIG. 1 shows a device for receiving and analysing capillary blood in an axial cut-out perspective view.

FIG. 2 shows a sample receiving unit of the device according to FIG. 1 in an initial position relative to a drive unit in a sectional axial cut-out.

FIGS. 3, 4, and 5 show various positions of advance of the sample receiving unit coupled to the drive unit for collecting blood from a finger pad in a drawing corresponding to FIG. 2.

DESCRIPTION OF SELECTED EMBODIMENTS

Figure 6:
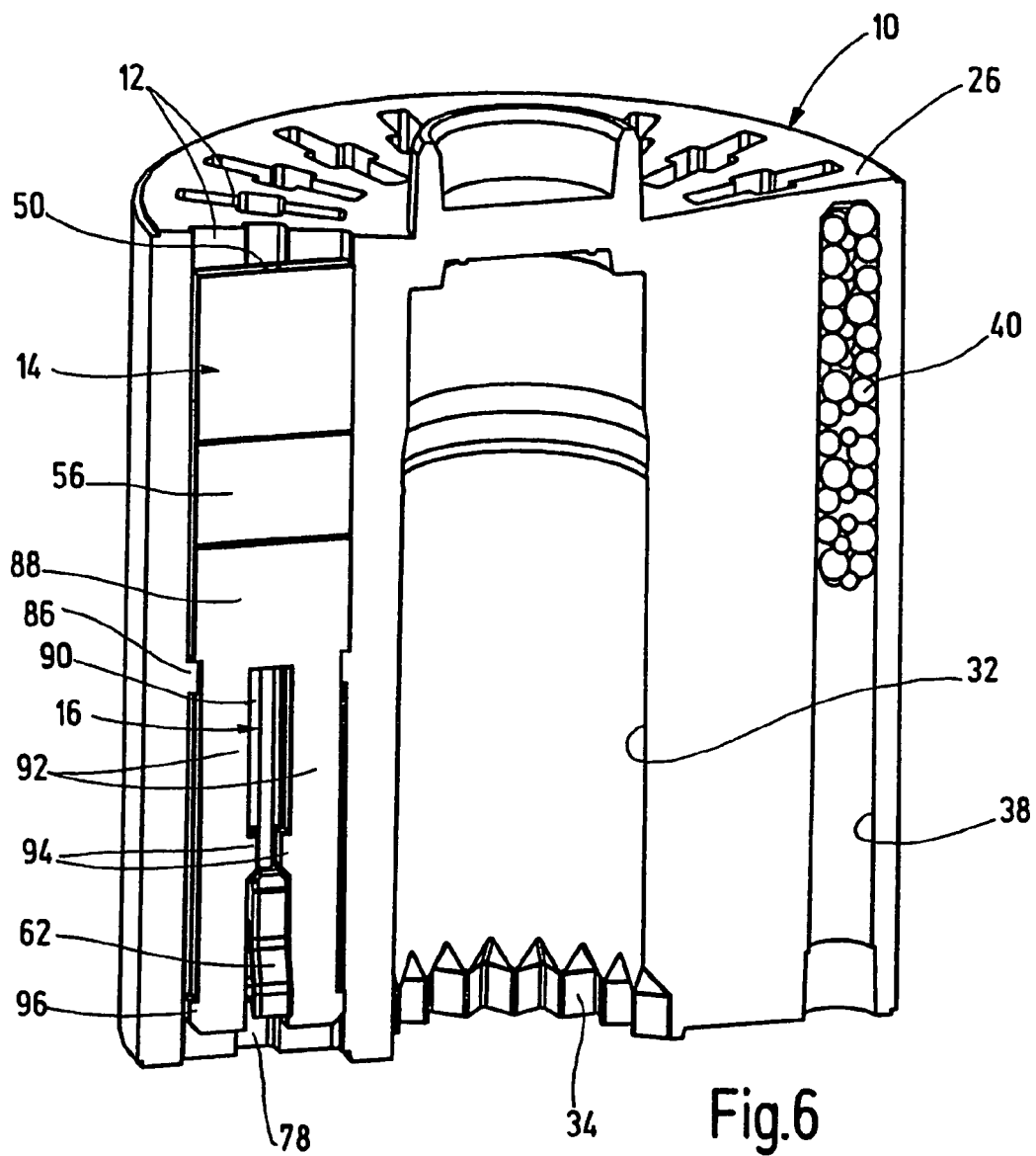
FIG. 6 shows another embodiment with a strip-shaped sample receiving unit formed from foil parts in a representation corresponding to FIG. 1.

For the purposes of promoting and understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates. It will be apparent to those skilled in the art that some of the features which are not relevant to the invention may not be shown for the sake of clarity.

The analytical device shown in the drawing is used to examine blood for patient self-monitoring especially for diabetics. The system comprises a storage container 10 having a plurality of guide chambers 12, each of the guide chambers having individually disposed sample receiving units 14 with an optionally integrated lancing unit 16 and coupling devices 18 to couple the sample receiving units or lancing units to a drive unit 20 for a forwards and backwards movement between the respective guide chamber 12 and a receiving site 22 in the area of a body part 24 for collecting blood.

As shown in FIG. 1 the container 10 is formed by a drum magazine 26 constructed as a cylindrical injection molded part made of plastic. The guide chambers 12 therein are distributed in the circumferential direction and extend axially continuously between an engagement opening 28 at the front end for the drive unit 20 and a discharge opening 30 at the opposite end for the sample receiving unit 14. The drum magazine 26 has a central bore 32 with peripheral gearing 34 for a stepping switch mechanism that is not shown in order to align a sample receiving unit 14 to be ejected in the feed axis 36 of the drive unit 20. Axial blind-end bores 38 to receive a desiccant 40 are arranged radially and offset to the outside. For protection against damaging environmental effects, the front ends of the guide chambers 12 are closed by a sealing foil 42 which is only partially shown in FIG. 1.

The sample receiving units 14 are thus only intended for single use as so-called "disposables". In the embodiment shown in FIG. 1, a hollow cylindrical injection molded part 44 made of plastic is provided for this purpose on which laterally projecting engaging means 46 of the coupling device 18 and stopping pieces 48 are molded thereon. An axial channel 50 serves as a mounting for the lancet 52 of the lancing unit such that it can be longitudinally displaced and at the same time serves at least in certain areas as a transport channel for the automatic capillary transport of the collected blood fluid from a receiving opening 54 pointing in the direction of advance to a test field 56. This test field 56 is constructed in a known manner to detect a component of the collected blood sample and in particular for a glucose test.

The tip 58 of the lancet 52 is displaced back relative to the front edge 60 of the sample receiving unit 14 in the feeding direction. The proximal end of the lancet is provided with a second engaging means 62 for a separate drive coupling that is mounted in the engaging means 46 of the sample receiving unit.

Accordingly the drive unit 20 shown in FIG. 2 has a double plunger 64 for coupling to the sample receiving unit 14 and the lancing unit 16. This is formed by an outer plunger 66 and an inner plunger 68 that can be telescoped therein. The transfer of reciprocating movement occurs by means of a form-fitting connection of each of the engaging means 46, 62 of the coupling device 18 as elucidated in more detail below.

The engaging means 46, 62 each comprise two holding claws 70, 72 which can be moved towards one another in a pincer-like (clamping) manner in order to grip behind an associated head piece 74, 76 of the outer plunger 66 or inner plunger 68 in a form-fitting manner. It shifts automatically into the engagement position as the plunger advances by tracking an associated guide block 78, 80 (FIGS. 1 and 5) where the guide block 78 for the outer holding claws 70 is formed by the narrow sides of the guide chambers 12 provided with tapers 77 whereas the inner flanks of the outer engaging means 46 form a corresponding guide block 80 for the holding claws 72 of the inner engaging means 62 of the lancing unit 16.

In the initial position shown in FIG. 2 of the drive unit 20, the drum magazine 26 can be rotated in a revolver-like manner in order to position the desired sample receiving unit 14 relative to the drive coupling. Then in a next step according to FIG. 3 the double plunger 64 is moved into the guide chamber 12 while piercing the sealing foil 42 over the engaging opening 28 and then butts against the front end of the engaging means 46, 62. After passing the bevels 77, the outer engaging means 46 firstly reaches its engaging position with the outer plunger 66 according to FIG. 4. The lateral guidance is supported in this process by the broad sides 82 of the guide chamber 12 which as gliding faces are adapted to the outer contour of the sample receiving unit 14. During the further advance, the projecting free front edge 60 of the sample receiving unit 14 pierces the sealing foil 42 over the ejection opening 30 during which the lancet tip 58 that is set back remains protected against accidental bending. As shown in FIG. 4, the advancing movement of the sample receiving unit 14 is stopped at the intended receiving site 22 at a predetermined distance to the finger pad 84 so as not to impede the escape of blood in the subsequent lancing process.

According to FIG. 5 the lancing process occurs with the outer engaging means 46 held in its engaging position secure from displacement by further advance of the inner plunger 68 whereby the inner engaging means 62 of the lancing unit 16 also reaches its engaging position after passing the bevel 85. The lancing depth is limited by the displacement distance that is available up to the indicated stop position of the inner engaging means 62 where the lancing speed should be as high as possible for a painless puncture.

After the puncture the lancet 52 and the sample receiving unit 14 are returned in the reverse sequence according to FIGS. 4 to 2. Only a microscopic amount (microlitre) of escaped blood is required at the puncture site which flows automatically by capillary action to the test field 56 via the capillary gap on the outer side of the lancet 52. Due to the form-fitting connection of the engaging means 46, 62 which also exists in the return direction, the sample receiving unit 14 can be retracted completely into the guide chamber 12 until finally the stop pieces 48 come to rest against the wall step 86 of the guide chamber 12 and the double plunger 64 is released again.

The embodiments described in the following are provided functionally with the same components with the same reference numerals as elucidated above such that to this extent reference can be made thereto.

Figure 7:
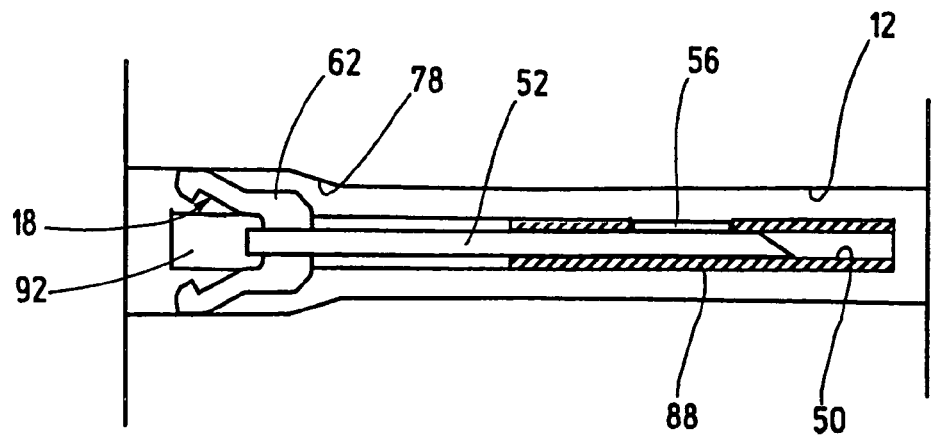
FIG. 7 shows the sample receiving unit according to FIG. 6 in a longitudinal middle section running perpendicular to the plane of the strip.

The embodiment example shown in FIGS. 6 to 10 differs primarily in that the sample receiving unit 14 is designed as a multilayer test strip 88. It is provided with a punched hole 90 in its proximal section to guide the engaging means 62 of the lancing unit 16 where the arms of the strip 92 formed in this manner have central and terminal stop shoulders 94, 96. As shown in FIG. 7, the lancet 52 is guided in an intermediate layer of the test strip 88 in a longitudinal slot 50 which also leads as a capillary flow path to the test field 56 and can be formed by punching or embossing. For technical manufacturing reasons, the test strip is not provided with a separate engaging means but as elucidated in the following its movement is controlled by the stop shoulders 94, 96 whose action is path-dependent whereas the lancing unit 16 tracks the guide block 78 of the guide chamber 12 by means of its associated engaging means 62.

Figure 8:
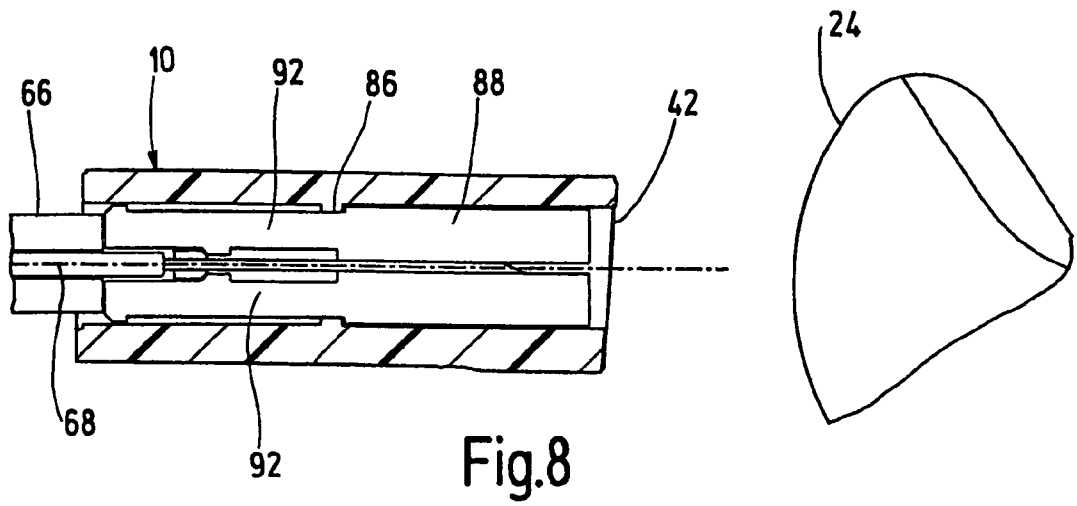
FIGS. 8, 9, and 10 show various positions of advance of the sample receiving unit in a representation corresponding to FIGS. 3, 4, and 5.
Figure 9:
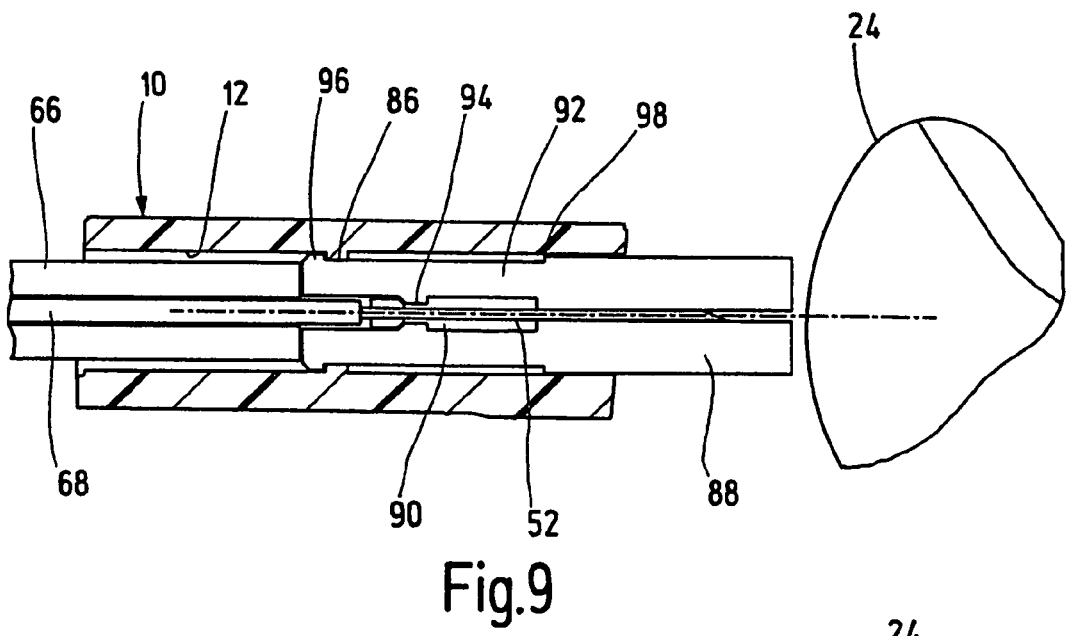
Figure 10:
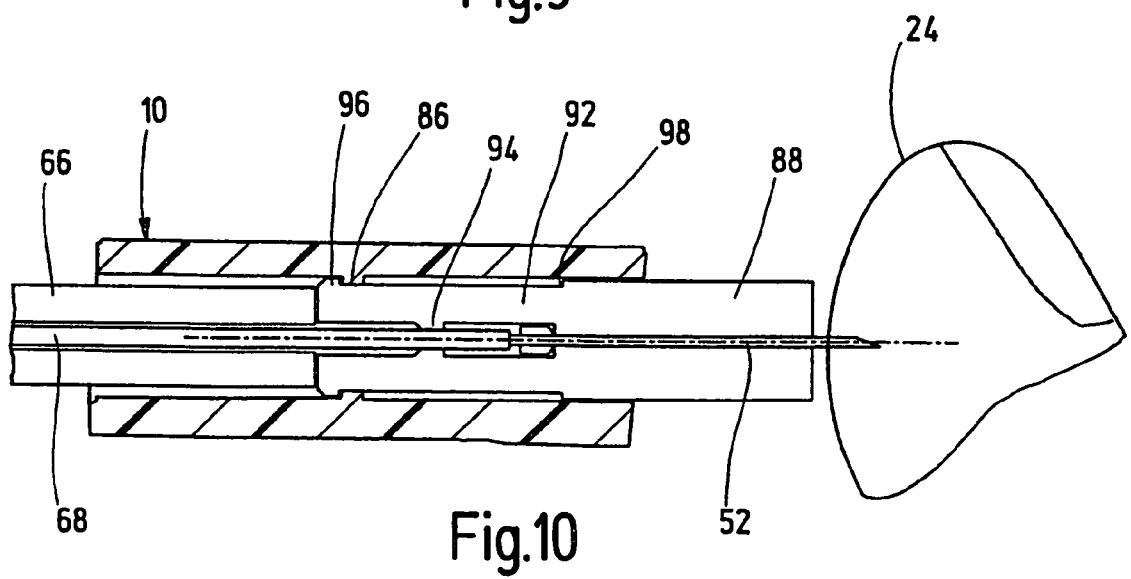

The sample collecting sequence shown in FIGS. 8 to 10 basically corresponds to the sequence according to FIGS. 3 to 5. A difference is that the outer plunger 66 only abuts the facing front edge of the test strip 88 in order to facilitate the piercing of the sealing foil 42 when it advances. In the stop position of the terminal outer stop shoulders 96 relative to the wall projection 86 that is effective on two sides shown in FIG. 9, the engaging means 62 can pass the inner stop shoulders 94 that face one another while elastically spreading the strip arm 92 whereby the outer stop shoulders 96 engage in wall recesses that are not shown. After the puncturing the retracted engaging means 62 that is coupled in a form-fitting manner with the inner plunger impinges against the inner stop shoulders 94 such that the test strip 88 is also returned into the guide chamber 12. The inner plunger 68 is in turn released by spreading the strip arms 92 in a stop position of the stop step 98 of the test strip 88 with the wall projection 86.

Figure 11:
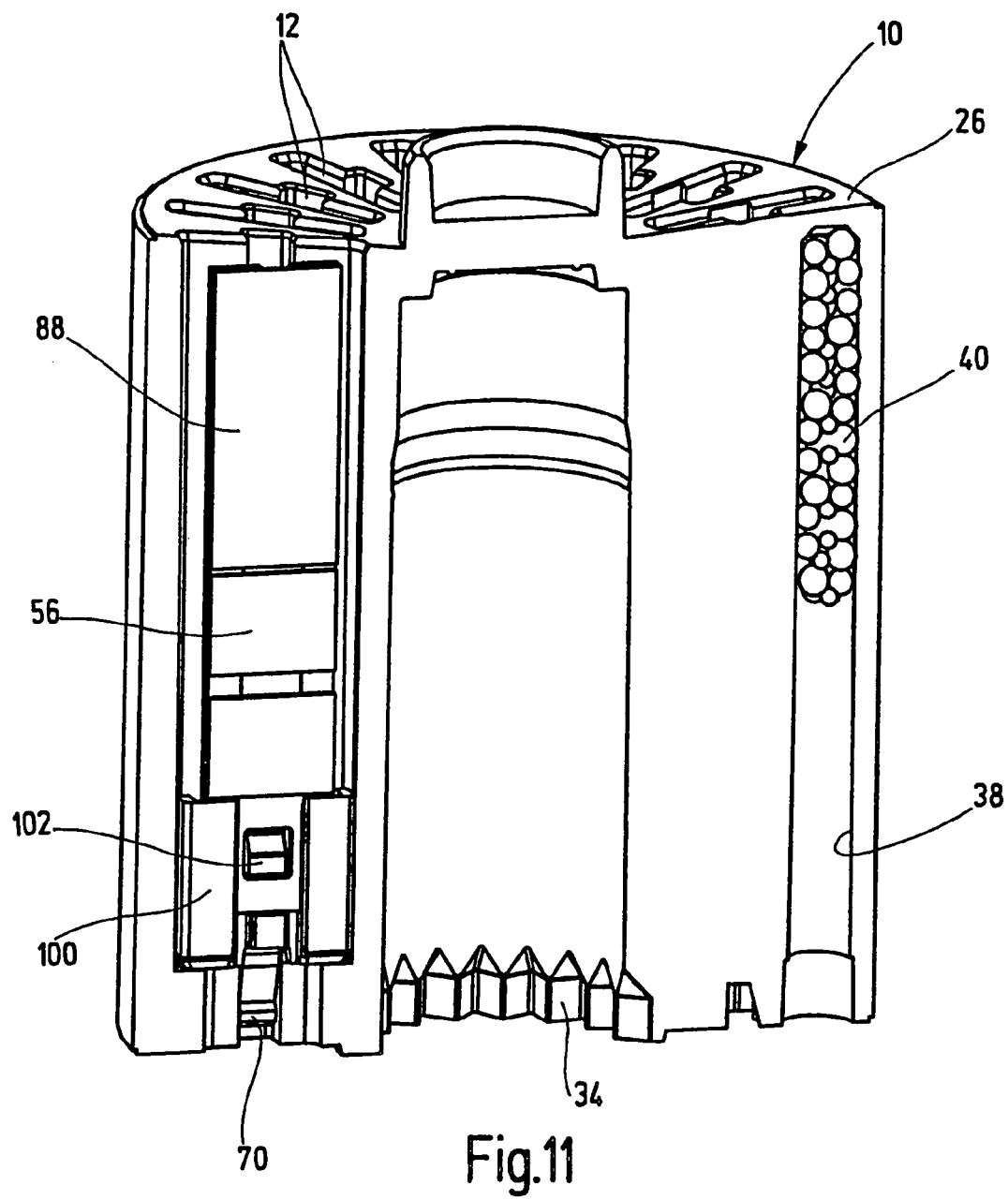
FIG. 11 shows another embodiment with a strip-shaped sample receiving unit supported on a carriage in a view corresponding to FIG. 6.
Figure 12:
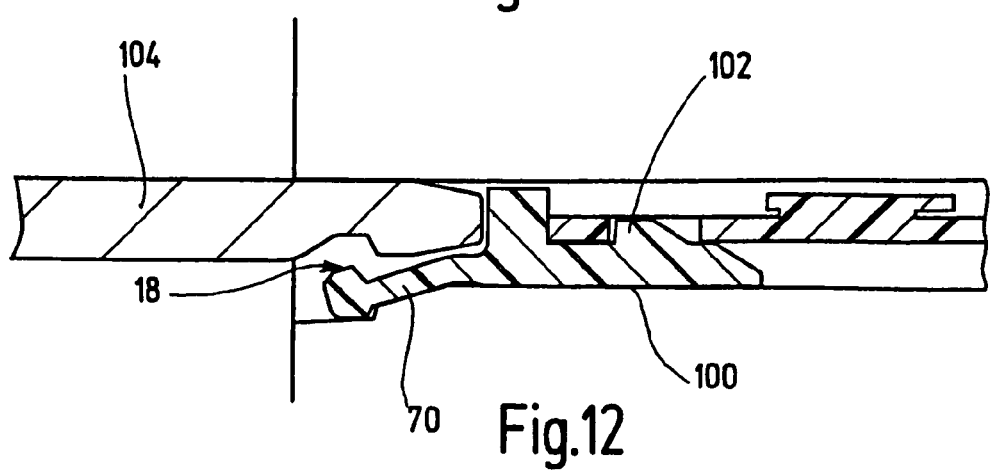
FIG. 12 shows a partial middle section of the sample receiving unit according to FIG. 11 perpendicular to the plane of the strip.

In the embodiment shown in FIGS. 11 and 12 the test strips 88 are held in a carriage 100 to improve the guidance and the carriage can be moved longitudinally in a draw-like manner in the respective guide chamber 12. The carriage 100 embraces an end section of the test strip 88 and is connected by means of a detent 102. For the form-fitting coupling to the single plunger 104, a single holding claw 70 of the carriage 100 is provided as an engaging means (FIG. 12). Instead of a lancing unit integrated into the test strip 88, a separate lancing aid (not shown) is used.

Figure 13:
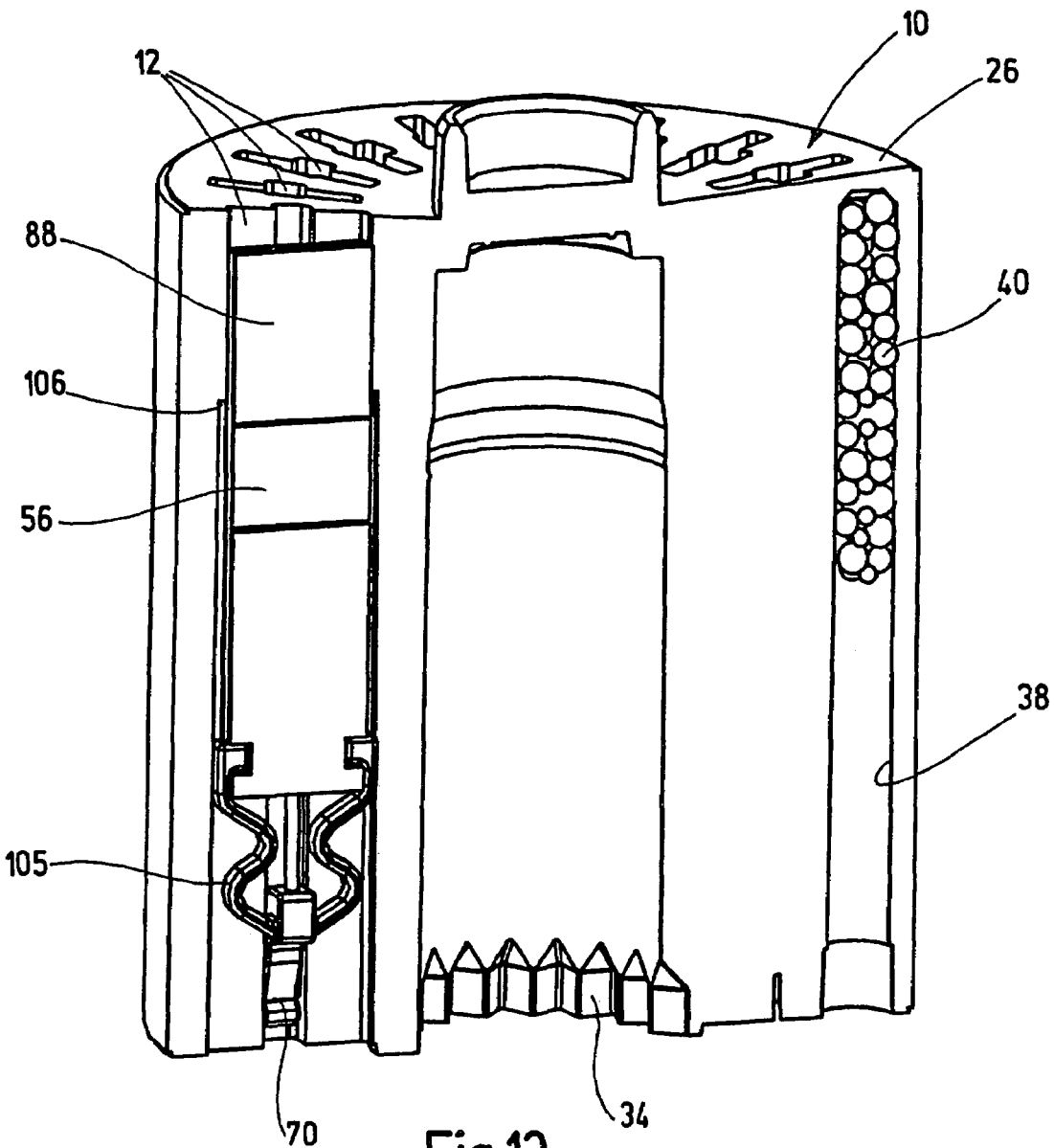
FIG. 13 shows another embodiment with a strip-shaped sample receiving unit supported on a spring member in a cut-out perspective view.
Figure 14:
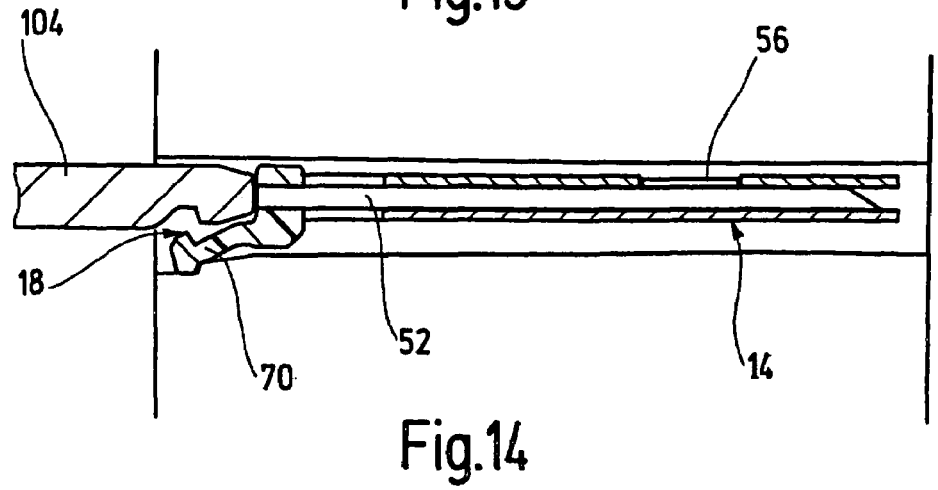
FIG. 14 shows the sample receiving unit according to FIG. 13 in a representation corresponding to FIG. 12.

In the embodiment according to FIGS. 13 and 14 a lancing unit 16 integrated into a test strip 88 can be connected in a form-fitting manner in accordance with the previously described carriage 100 for a reciprocating motion by means of an individual holding claw 70 as a engaging means with a single drive plunger 104. A spring clip 105 is provided to transfer the movement onto the test strip 88. As it advances a stop position of the foil strip 88 is reached relative to a wall step 106 in which the lancet 52 can be moved further against the restoring force of the spring clip 104 for puncturing.

As also in the case of the embodiment example of FIG. 7 the effective cross-section of the transport channel 50 is limited to a ring gap by the outer diameter of the lancet 52. Since the lancet does not lie exactly in the middle due to the effect of gravity, the gap is larger in the area facing away from the bearing side. This area can be additionally extended by an appropriate design in order to steer the blood flow and to guide it onto the test field 56 via a lateral outlet opening.

Figure 15:
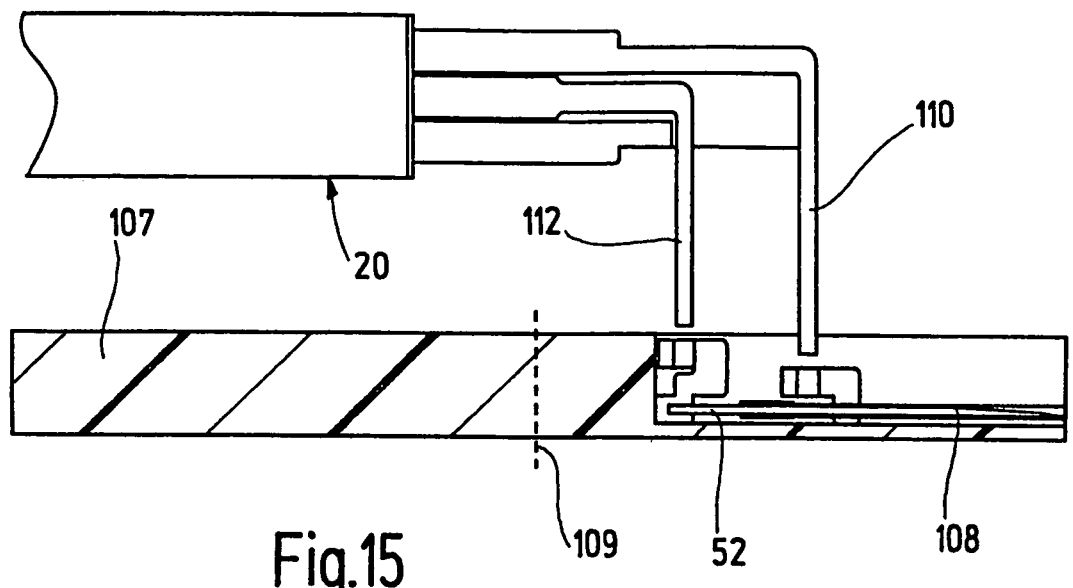
FIG. 15 shows an embodiment of a disk-shaped device for receiving and examining blood samples in an axial section.
Figure 16:
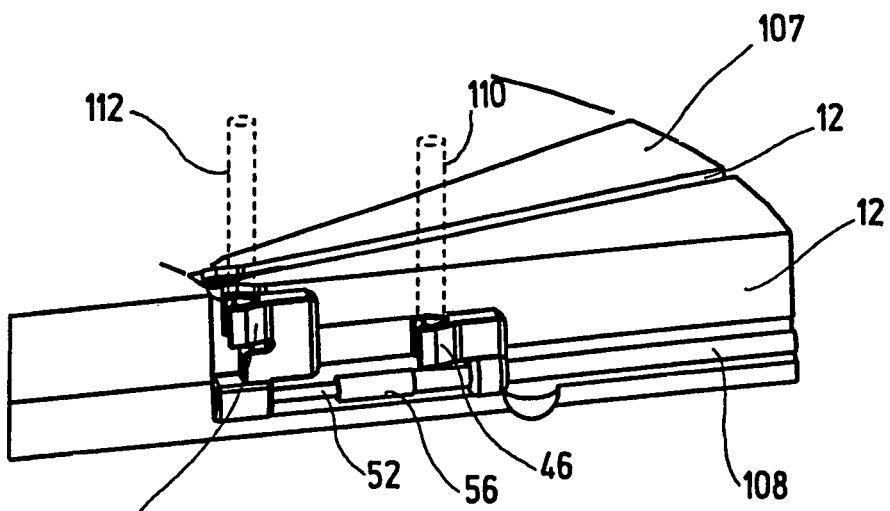
FIGS. 16 and 17 show the device according to FIG. 15 in a starting position and in a removal position of a sample receiving unit that can be pushed out radially in a partial perspective view.
Figure 17:
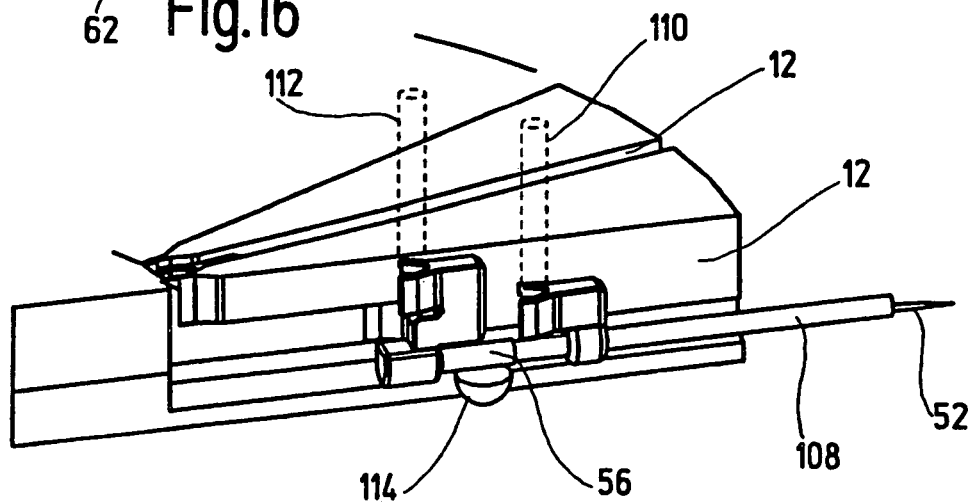
Figure 18:
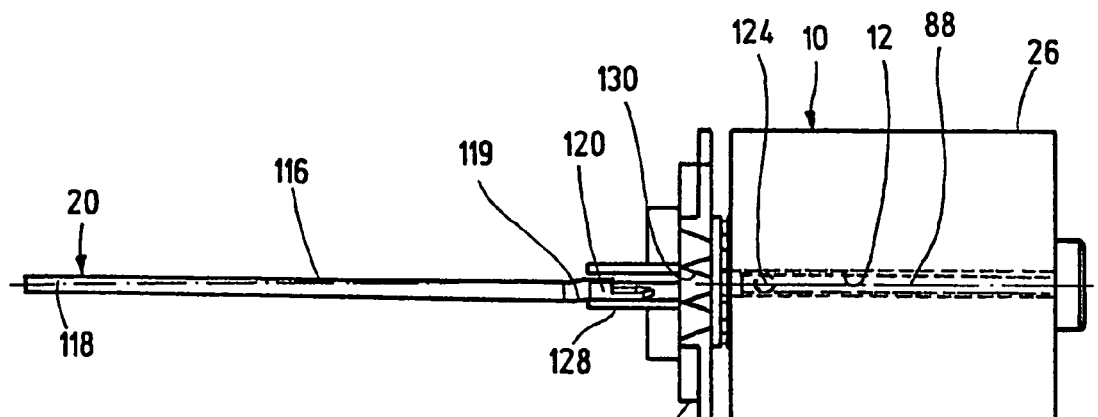
FIG. 18 shows another embodiment with a hooked plunger for an advancing and returning movement of a test strip in a longitudinal section.
Figure 19:
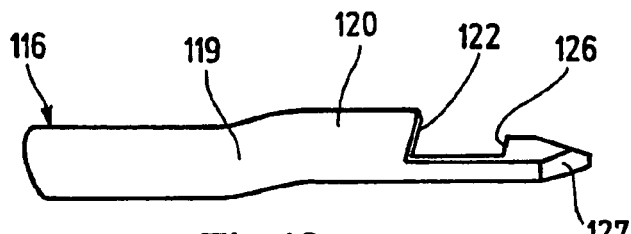
FIG. 19 shows a cut-out side view of a head piece of the cranked hooked plunger.

The embodiment of FIGS. 15 to 17 comprises a flat disk-shaped magazine 107 as a container 10 in which the guide chambers 12 extend radially. Hollow needles 108 are stored radially therein in a displaceable manner as sample receiving units 14. The hollow needles or sample tubes 108 in turn form a guide for a separately movable lancet 52. The drive coupling is by means of engaging means 46, 62 which can be moved into the front advance position shown in FIG. 12 by means of angled push rods 110, 112 which successively engage parallel to the disk axis in the open-ended guide chambers 12 of the drive unit 20. The collected blood flows via the hollow needle 108 axially to the sleeve-shaped test field 56 whose response to an analyte can be optically detected through the calotte-shaped window 114.

In the embodiment shown in FIGS. 18 to 24 the coupling device 18 has a hooked plunger 116 that can be coupled to the test strips 88 in a drum magazine 26 which is driven at its proximal end 118 for a reciprocating movement. The distal end of the hooked plunger 116 is provided with a hook head 120 that is angled over a knee piece 119. In accordance with FIG. 19 this has a driving flank 122 that abuts against the rear end of a test strip 88 to advance the strip and a pulling flank 126 that can engage in a recess 124 of the test strip 88 to return the strip. In order to secure the stop position and to facilitate the disengagement, the flanks 122, 126 are sloped in the direction of advance towards their free lateral edge. A spiked projection 127 molded onto the front end of the hook head 120 with its tip pointing in the direction of advance enables an easy piercing of a foil which tightly seals the guide chamber 12.

The hooked plunger 116 is mounted in a guide sleeve 128 which can be aligned with the desired guide chamber by means of a drum or index wheel 132 provided with conical centering openings 130 at the front end of the drum magazine 26.

Figure 20:
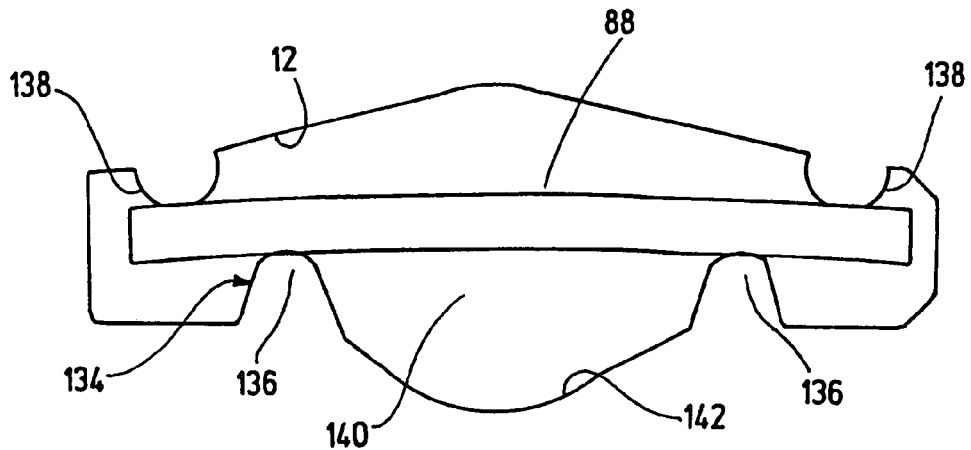
FIG. 20 shows a view of the rear side of a test strip clamped in a guide chamber.
Figure 21:
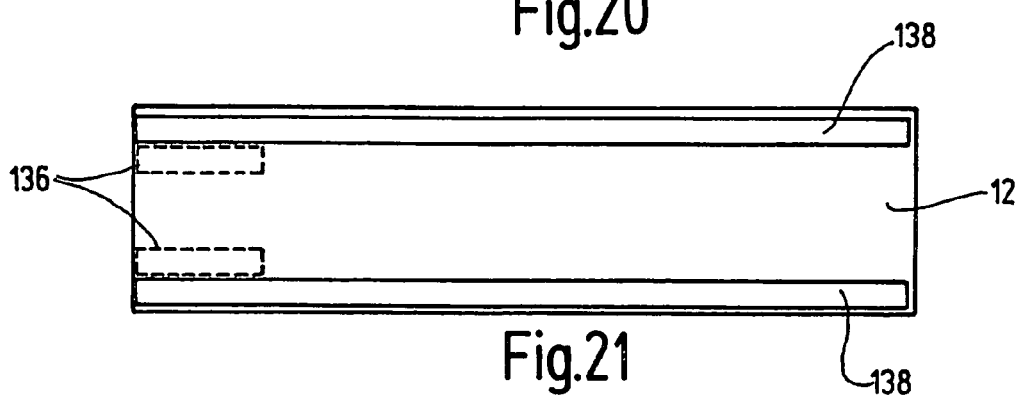
FIG. 21 shows a longitudinal section through the guide chamber according to FIG. 20 and FIGS. 22, 23, and 24 show various positions of advance of the hooked plunger that can hook onto the test strip in a perspective view.

As best shown in FIGS. 20 and 21 the proximal end sections of the test strips 88 are held in a detachable manner in their respective guide chamber 12 by a clamping structure 134. For this purpose, the clamping structure 134 has two laterally spaced clamping cams 136 projecting into the guide chamber 12 which interact with outwardly offset guide ribs 138 extending longitudinally in the guide chamber 12. In this process the test strip 88 that is clamped at its end is curved outwards at right angles while bending elastically such that the test strip provides an extended engagement cross-section 140 for the hooked plunger 116.

Figure 22:
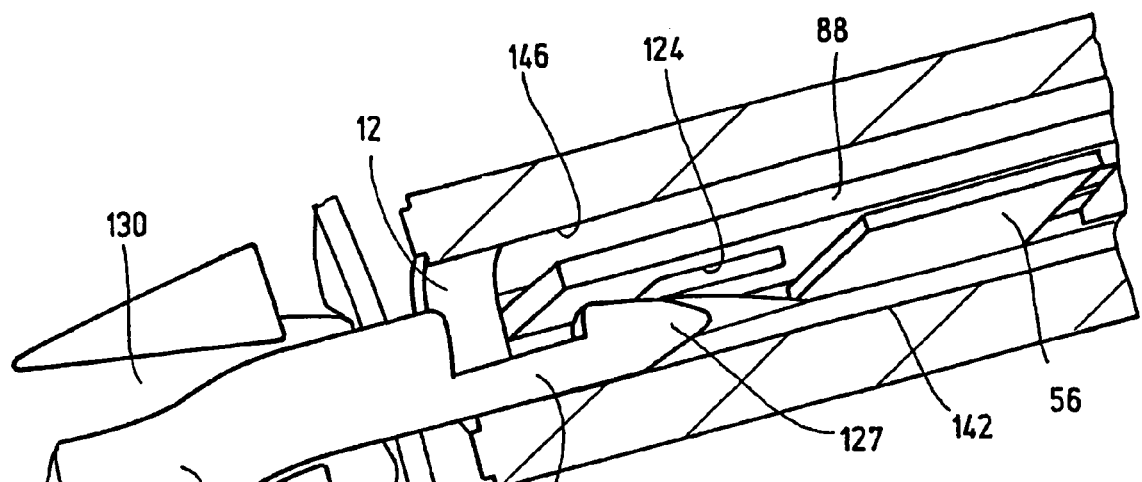
Figure 23:
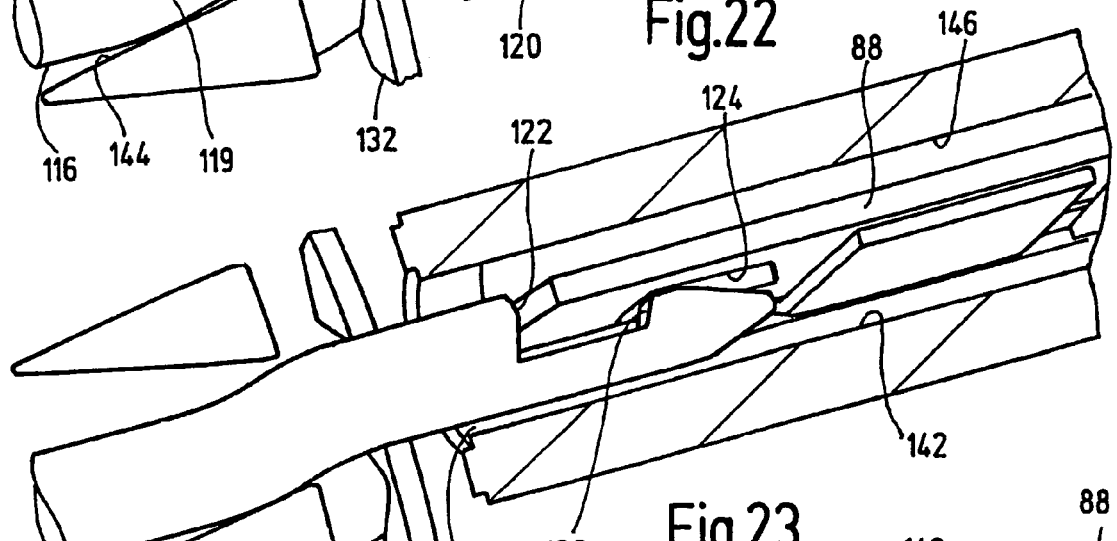
Figure 24:
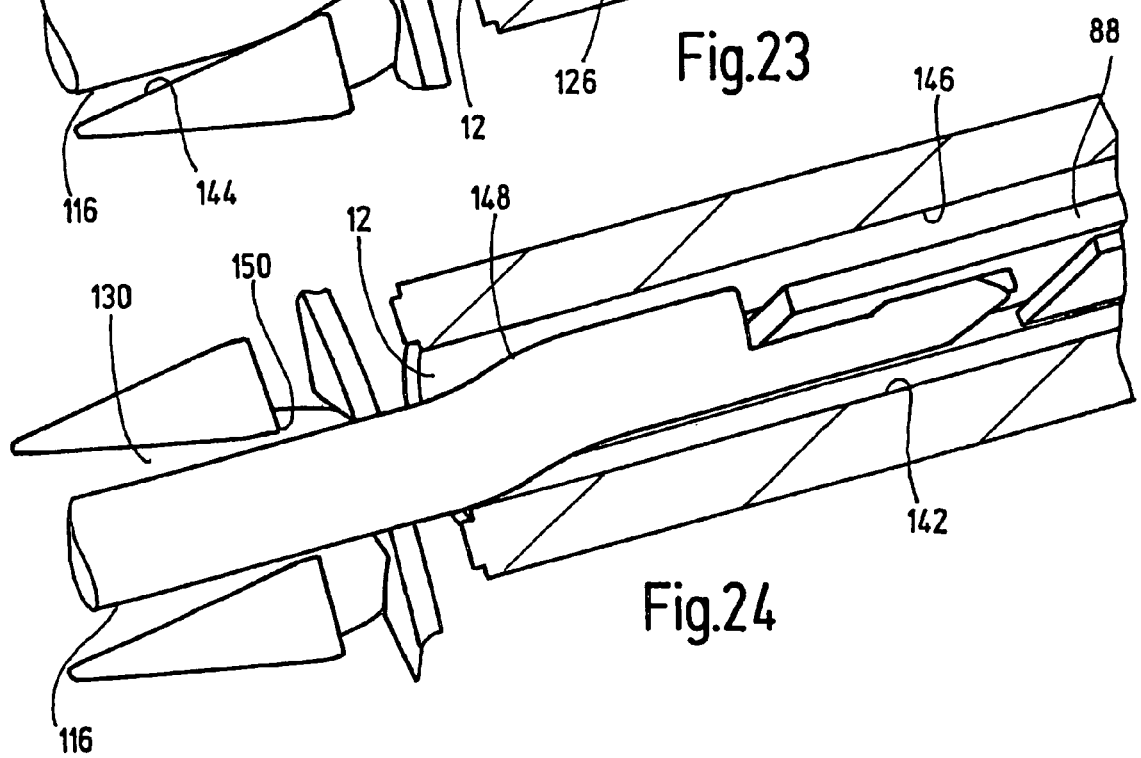

FIGS. 22 to 24 illustrate the controlled guidance of the hooked plunger 116 during the engagement and disengagement process. The angling of the plunger displaces the guiding cone 130 relative to the central axis of the guide chamber in the circumferential direction of the drum wheel 132 whereby the hook head 120 projects laterally towards the test strip 88. When the spiked projection 127 is inserted, a lower wall 142 of the guide chamber 12 forms a guide surface until the knee piece 119 runs up against the bevel 144 of the guide cone 130. As a result the hook head 120 is lifted during a pivoting movement of the hooked plunger 116 and the pulling flank 126 engages behind the edge of the recess 124 whereas the pushing flank 122 abuts against the end of the strip (FIG. 23). As it advances further in the stop position of the pushing flank 122, the clamping force of the clamping structure 134 is overcome by the higher driving force of the drive unit (not shown) whereby the test strip 88 gets free of the clamping projections 136 and finally reaches the receiving position. In this process, the cranked hooked plunger is guided and secured between the opposing walls 142 and 146 of the guide chamber 12.

During its return movement the upper portion 148 of the knee piece 119 of the hooked plunger 116 impinges on the upper cone edge 150 of the guide cone 130 and as a result is pressed downwards until it disengages in the clamping position of the test strip 88. The slope of the pulling flank 126 ensures that the blocking action is less than the maximum pulling force and the hooked plunger 116 again disengages from the recess 124. The guide sleeve 128 ensures that the hook head 120 does not hook onto the drum wheel 132 during the advance and return. The consumed test strip 88 is held clamped in the correct position and it is possible to advance to the next guide chamber in the magazine 26.

The invention claimed is:

1. Device for receiving a body fluid for analytical purposes comprising: a container; at least one sample receiving unit for a single-use test that can be pushed out of a guide chamber of the container by means of a drive unit and to which the body fluid can be applied at a receiving site; wherein the container is designed as a magazine for storing a plurality of sample receiving units;
   a lancing unit constructed as a lancet is integrated in the sample receiving unit to carry out a lancing movement towards a body part of a test person;
   means for separately retracting the sample receiving unit and the lancing unit into the guide chamber; wherein the means for separately retracting the sample receiving unit and the lancing unit includes a double plunger incorporated into the drive unit;
   the double plunger having an inner plunger received inside an outer plunger in a telescoping manner;
   the sample receiving unit and the lancing unit each having holding claws configured to move in a clamping manner to couple the sample receiving unit to the drive unit for a forwards and backwards movement between the guide chamber and the receiving site;
   the guide channel having outer guide blocks positioned to clamp the holding claws of the sampling unit to the outer plunger when the outer plunger is extended; and
   the sample receiving unit having inner guide blocks positioned to clamp the holding claws of the lancing unit to the inner plunger when the inner plunger is extended.

2. Device according to claim 1, wherein the drive unit and the sample receiving unit are separated from one another in an initial position.

3. Device according to claim 1, wherein the drive unit and sample receiving unit couple in a form fitting manner.

4. Device according to claim 3, wherein the holding claws are movable in a distance-dependent manner between a release position and an engaging position during the forwards and backwards movement.

5. Device according to claim 3, wherein the outer and inner guide blocks are each formed by an inclined bevel that can be tracked by the engaging means.

6. Device according to claim 3, wherein the holding claws are located at a proximal end of the sample receiving unit.

7. Device according to claim 3, wherein at least one of the holding claws is shifted into an engaging position under its own tension.

8. Device according to claim 3, wherein the double plunger has a head member and that the holding claws automatically engages the head member of the double plunger when the double plunger is advanced axially.

9. Device for receiving a body fluid for analytical purposes comprising a container and at least one sample receiving unit for a single-use test that can be pushed out of a guide chamber of the container by means of a drive unit and to which the body fluid can be applied at a receiving site, wherein a lancing unit is integrated into the sample receiving unit to carry out a lancing movement towards a body part containing the body fluid;
   wherein the drive unit has a double plunger that can be longitudinally moved therein to separately extend and retract the sample receiving unit and lancing unit;
   the double plunger having an inner plunger received inside an outer plunger in a telescoping manner;
   the sample receiving unit and the lancing unit each having holding claws configured to move in a clamping manner;
   the guide channel having guide blocks positioned to clamp the holding claws of the sampling unit to the outer plunger when the outer plunger is extended; and
   the sample receiving unit having guide blocks positioned to clamp the holding claws of the lancing unit to the inner plunger when the inner plunger is extended.

10. Device according to claim 9, wherein the lancing unit can be displaced in a guide of the sample receiving unit in its direction of movement.

11. Device according to claim 9, wherein the lancing unit can puncture the body part at a predetermined distance to a free front area of the sample receiving unit.

12. Device according to claim 9, wherein the lancing unit can be coupled in a form-fitting manner to the drive unit by means of the holding claws for a reciprocating lancing movement.

13. Device according to claim 9, wherein the drive unit has a control device to control the sequence of movements of the sample receiving unit and/or lancing unit.

14. Device according to claim 9, wherein the sample receiving unit has limit stops for the lancing unit formed by projecting edges of the body.

15. Device according to claim 1, wherein the sample receiving unit can be moved in a sliding guide of the guide chamber.

16. Device according to claim 1, wherein the sample receiving unit has an analytical test element to examine the body fluid.

17. Device according to claim 1, wherein the sample receiving unit has a capillary active transport channel for the body fluid.

18. Device according to claim 17, wherein the transport channel is formed by a ring gap between a lancet and a wall area of the sample receiving unit surrounding the lancet.

19. Device according to claim 17, wherein the transport channel ends on an analytical test field via a lateral outlet in the transport area.

20. Device according to claim 1, wherein the guide chamber is closed by a sealing foil at least in the area of an ejection opening and that the sample receiving unit has a free end area facing the direction of advance to pierce the sealing foil.

21. Device according to claim 1, wherein the sample receiving unit is constructed as a test strip or as an injection molded test body in particular for examining blood.

22. Device according to claim 1, wherein the container as a drum magazine has a plurality of guide chambers running axially each for one sample receiving unit that are distributed in the circumferential direction.

23. Analytical instrument and in particular transportable hand device for medical diagnostics, comprising a device for receiving a body fluid according to claim 1.

24. Sample receiving unit for a body fluid in particular a test strip or tube having coupling means for a form-fitting drive coupling in order to push it out of and return it into a guide chamber for use in a device according to claim 1.

25. Device according to claim 9, further comprising:
   the double plunger having an inner plunger received inside an outer plunger in a telescoping manner;
   the sample receiving unit and the lancing unit each having holding claws configured to move in a clamping manner;

the guide channel having guide blocks positioned to clamp the holding claws of the sampling unit to the outer plunger when the outer plunger is extended; and the sample receiving unit having guide blocks positioned to clamp the holding claws of the lancing unit to the inner plunger when the inner plunger is extended.

26. A device for receiving a body fluid for analytical purposes, comprising:

a container defining one or more guide chambers;

a unitary disposable received in each of the guide chambers, the disposable including a sample receiving unit integrated with a lancing unit, the lancing unit being moveable relative to the sample receiving unit;

a drive unit configured to extend and retract the sample receiving unit and the lancing unit in a separate manner relative to the guide chamber;

a coupling device configured to couple the drive unit and the disposable in a form fitting manner to facilitate the extension and retraction of the sample receiving unit and the lancing unit in the separate manner; and wherein the coupling device includes holding claws on both the sample receiving unit and the lancing unit configured to move in a clamping manner.

27. The device of claim 26, further comprising:

the drive unit including a double plunger;

the double plunger including an inner plunger received inside an outer plunger in a telescoping manner;

the inner plunger and the outer plunger both having a head piece; and the holding claws being configured to grip the head pieces of the inner plunger and the outer plunger in an form fitting manner to facilitate separate retraction.

28. The device of claim 26, wherein the drive unit includes angled push rods.

29. The device of claim 26, wherein the sample receiving unit has a test field to analyze the body fluid.

30. The device of claim 26, wherein the container is a drum.

31. The device of claim 26, wherein the container is a disc.

32. A method, comprising:

coupling a drive unit to a sample receiving unit that includes an integrated lancing unit by coupling the drive unit in a form fitting manner to at least the lancing unit, wherein the sample receiving unit and the lancing unit are integrated together to form a unitary disposable;

extending the sample receiving unit out of a guide chamber of a container with a drive unit;

cutting an incision in skin with the lancing unit by extending the lancing unit from the sample receiving unit with the drive unit;

retracting the lancet from the incision with the drive unit;

collecting body fluid from the incision with the sample receiving element after said retracting the lancet;

retracting the sample receiving unit into the guide chamber with the drive unit after said collecting the body fluid;

wherein said coupling the drive unit to the sample receiving unit further includes coupling the drive unit in a form fitting manner to the sample receiving unit;

wherein the drive unit includes a double plunger that has an inner plunger received inside an outer plunger in a telescoping manner;

wherein the sample receiving unit and the lancing unit each have holding claws configured to move in a clamping manner;

wherein the guide channel and the sample receiving unit each have guide blocks; and wherein said coupling the drive unit to the sample receiving unit includes clamping the holding clamps of the lancing unit to the inner plunger with the guide blocks in the sample receiving unit by extending the inner plunger, and clamping the holding clamps of the sampling unit to the outer plunger with the guide blocks in the guide channel by extending the outer plunger.

33. The method of claim 32, further comprising:

disengaging the drive unit from the sample receiving unit after said retracting the sample receiving unit into the guide chamber.

34. The method of claim 33, wherein said disengaging the drive unit includes:

unclamping the holding clamps of the lancing unit from the inner plunger by retracting the inner plunger; and unclamping the holding clamps of the sampling unit from the outer plunger by retracting the outer plunger.

35. The method of claim 32, further comprising:

positioning the drive unit to engage a second sampling unit by indexing the container.

* * * * *

UNITED STATES PATENT AND TRADEMARK OFFICE
CERTIFICATE OF CORRECTION

PATENT NO.       : 7,740,599 B2                                                    Page 1 of 1
APPLICATION NO.  : 11/178810
DATED            : June 22, 2010
INVENTOR(S)      : Klaus-Dieter Sacherer It is certified that error appears in the above-identified patent and that said Letters Patent is hereby corrected as shown below:

Col. 10, line 59, to Col. 11, line 6, delete claims 24 and 25

Signed and Sealed this

Fifth Day of October, 2010

David J. Kappos
*Director of the United States Patent and Trademark Office*